United States Patent
Robinson et al.

(10) Patent No.: US 11,737,717 B2
(45) Date of Patent: Aug. 29, 2023

(54) SYSTEMS AND METHODS FOR GUIDING A PATIENT DURING IMAGING PROCEDURES

(71) Applicant: Hologic, Inc., Marlborough, MA (US)

(72) Inventors: John W. Robinson, Bethel, CT (US); Kenneth Defreitas, Patterson, NY (US); Adrian Hunsdon, Southbury, CT (US); Rachel Chandler, Newark, DE (US); Ashwini Kshirsagar, Santa Clara, CA (US); David Wolff, Hockessin, DE (US); Alan Rego, Woodbury, CT (US)

(73) Assignee: Hologic, Inc., Marlborough, MA (US)

( * ) Notice: Subject to any disclaimer, the term of this patent is extended or adjusted under 35 U.S.C. 154(b) by 172 days.

(21) Appl. No.: 17/407,452

(22) Filed: Aug. 20, 2021

(65) Prior Publication Data

US 2022/0087629 A1    Mar. 24, 2022

Related U.S. Application Data

(60) Provisional application No. 63/082,248, filed on Sep. 23, 2020.

(51) Int. Cl.
*A61B 6/00* (2006.01)
*A61B 6/04* (2006.01)

(52) U.S. Cl.
CPC .............. *A61B 6/46* (2013.01); *A61B 6/0414* (2013.01); *A61B 6/4435* (2013.01); *A61B 6/502* (2013.01); *A61B 6/548* (2013.01)

(58) Field of Classification Search
CPC ....... A61B 8/0825; A61B 6/502; A61B 6/025; A61B 6/0414; A61B 6/03; A61B 90/11; A61B 90/17; A61B 2017/3414; A61B 2090/3908; A61B 5/4312; A61B 5/708; A61B 5/0091
See application file for complete search history.

(56) References Cited

U.S. PATENT DOCUMENTS

| 2009/0080186 A1 | 3/2009 | Helmreich et al. |
| 2014/0180082 A1* | 6/2014 | Evans ............... A61B 6/502 600/436 |

FOREIGN PATENT DOCUMENTS

| JP | 2013/066784 A | 4/2013 |
| WO | 2016/093655 A1 | 6/2016 |
| WO | 2019/035064 A1 | 2/2019 |

OTHER PUBLICATIONS

European Extended Search Report in Application 21198095.8, dated Feb. 17, 2022, 12 pages.
European Extended Search Report in Application 21198095.8, dated Jul. 1, 2022, 13 pages.

* cited by examiner

*Primary Examiner* — Don K Wong
(74) *Attorney, Agent, or Firm* — Merchant & Gould P.C.

(57) ABSTRACT

A method of imaging a breast of a patient using an imaging system includes applying, with a first component of the imaging system, a compressive force to the breast. A second component of the imaging system is positioned in a start position. The imaging system sends a first guidance signal to the patient. An imaging procedure of the breast is performed with the second component of the imaging system. Subsequent to performing the imaging procedure, a second guidance signal is sent to the patient.

20 Claims, 6 Drawing Sheets

SYSTEMS AND METHODS FOR GUIDING A PATIENT DURING IMAGING PROCEDURES

CROSS-REFERENCE TO RELATED APPLICATIONS

This application claims priority to, and the benefit of, U.S. Provisional Patent Application No. 63/082,248, filed Sep. 23, 2020, the disclosure of which is hereby incorporated by reference herein in its entirety.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; (4) brings breast tissues out from the chest wall into the imaging exposure field and thus allows for more tissue imaging; and (5) spreads out the fibro glandular tissue over large area in order to avoid caner tissue being hidden in the middle of normal tissue. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may also potentially dissuade patients from getting screened for breast cancer. This discomfort may also cause a patient to move during imaging, inadvertently hold their breath or panic breathe, or otherwise take an action that may be detrimental to the images or themselves. While technologists are trained to guide and reassure patients, the technologist is often focused on controlling the imaging procedure itself and may be distracted.

SUMMARY

In one aspect, the technology relates to a method of imaging a breast of a patient using an imaging system, the method including: applying, with a first component of the imaging system, a compressive force to the breast; positioning a second component of the imaging system in a start position; sending, from the imaging system, a first guidance signal; performing an imaging procedure of the breast with the second component of the imaging system; and subsequent to performing the imaging procedure, sending a second guidance signal. In an example, the first guidance signal includes at least one of a visible light and an audible noise. In another example, the first guidance signal comprises a light of a first color and the second guidance signal includes a light of a second color different than the first color. In yet another example, performing the imaging procedure includes emitting a single x-ray emission. In still another example, performing the imaging procedure includes emitting a plurality of x-ray emissions.

In another example of the above aspect, the first guidance signal includes a first sound and the second guidance signal includes a second sound different than the first sound. In an example, the method further includes, during performance of the imaging procedure, sending a third guidance signal.

In another aspect, the technology relates to a breast imaging system including: a gantry including a patient side and a rear; a compression system movably secured to the patient side of the gantry, wherein the compression system includes a breast support platform and a compression arm movable relative to the breast support platform; a tube head rotatably connected to the gantry; and a patient guidance module for sending at least one of a visual guidance signal and an audible guidance signal to the patient when a breast of the patient is compressed by the compression system. In an example, the patient guidance module includes a light emitting element disposed on the rear of the gantry.

In another aspect, the technology relates to a method of guiding a patient action during a procedure with a breast imaging system, the method including: detecting a condition of a first component of the breast imaging system, wherein at least a portion of the breast imaging system is in contact with a breast of the patient; and sending, from the breast imaging system, a guidance signal to the patient based at least in part on the detected condition, wherein the guidance signal is associated with an action to be taken by the patient. In an example, the method further includes, prior to detecting the condition, receiving, at the breast imaging system, a procedure initiation signal, wherein the procedure initiation signal is sent from a physical location remote from the breast imaging system. In another example, the method further includes, subsequent to receiving the procedure initiation signal and prior to detecting the condition, moving a second component of the breast imaging system to a start position. In yet another example, the first component is disposed within the second component. In still another example, the first component includes an x-ray tube.

In another example of the above aspect, the detected condition includes a voltage reading. In an example, the guidance signal includes an audible sound. In another example, the audible sound is non-verbal. In yet another example, the guidance signal is an emitted light. In still another example, the emitted light is emitted from a light emitting element outside a line of sight of the patient when the portion of the breast imaging system is in contact with the breast of the patient.

DETAILED DESCRIPTION

Figure 1A:
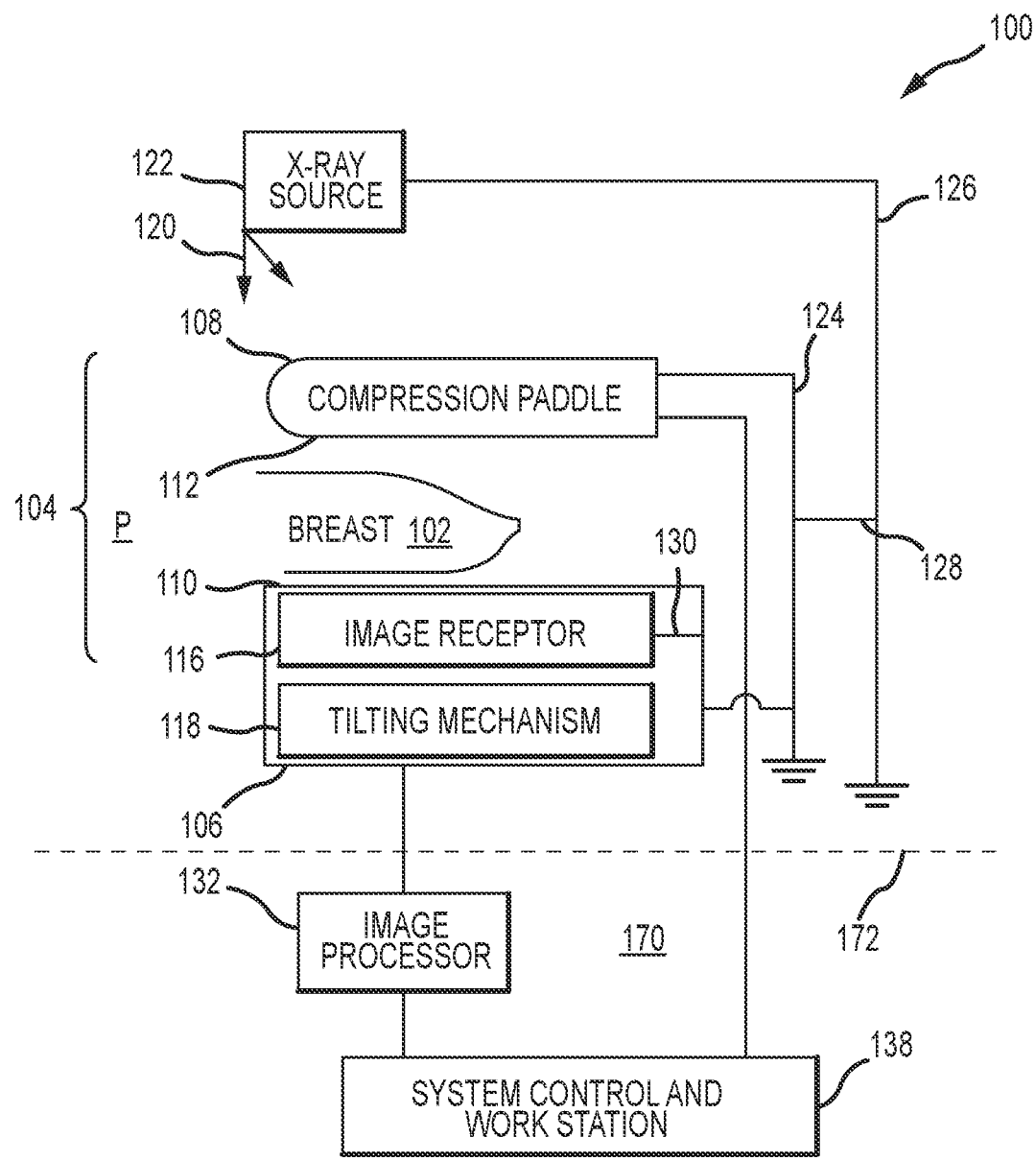
FIG. 1A is a schematic view of an exemplary imaging system.
Figure 1B:
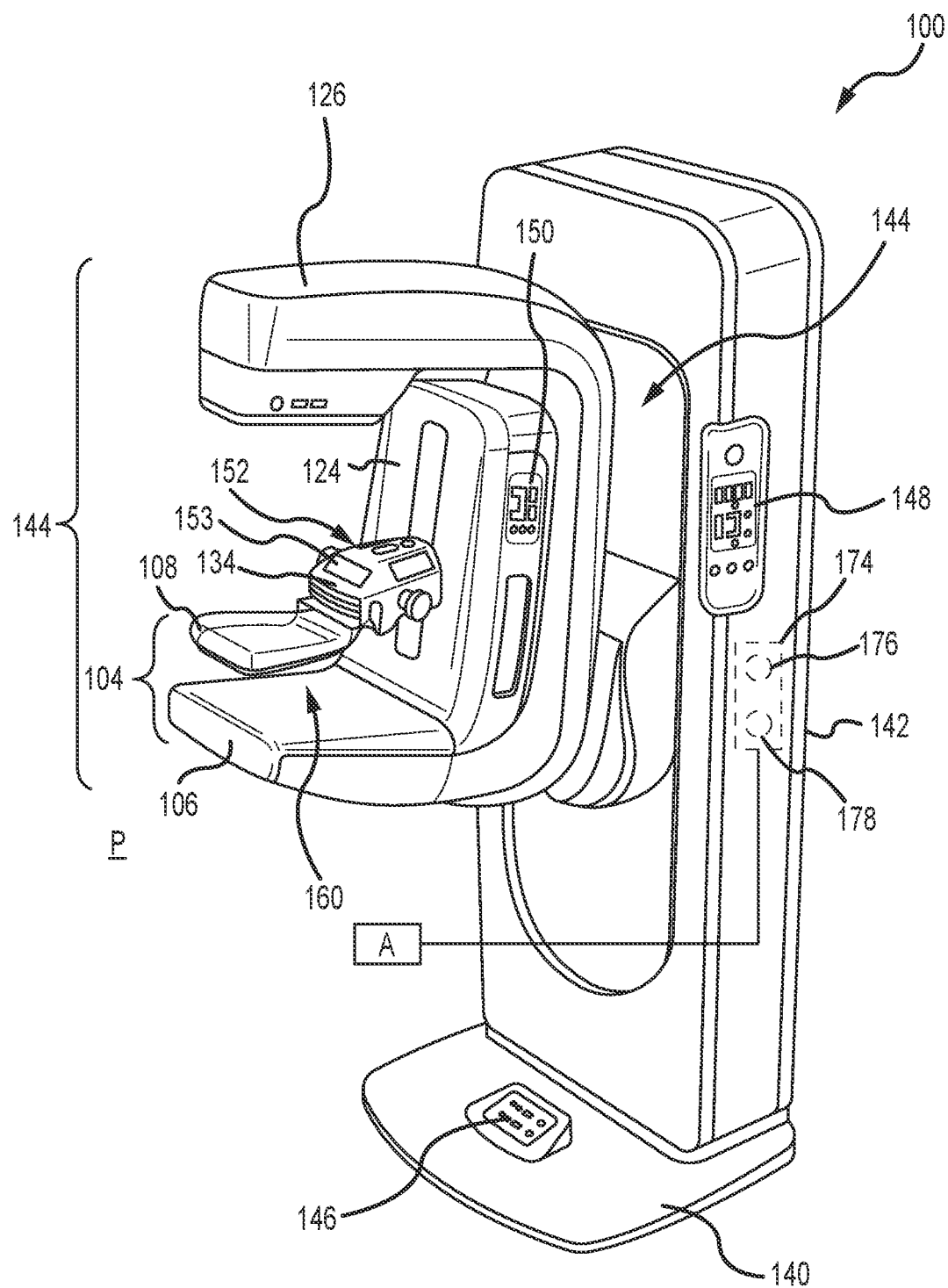
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, not every element described below is depicted in both figures. The imaging system 100 immobilizes a patient's breast 102 for x-ray imaging (either or both of mammography and tomosynthesis) via a breast compression immobilizer unit 104 that includes a static breast support platform 106 and a moveable paddle 108. Different paddles, each having different purposes, are known in the art. Certain examples paddles are also described herein for context. The breast support platform 106 and the paddle 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. Either or both of these compression surfaces 110, 112 may be rigid plastic, a flexible plastic, a resilient foam, a mesh or screen, and so on. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images. In examples, the image processor 132 and work station unit 138 may be disposed at a physical location remote from the imaging system 100 itself. Often, these components may be disposed in a remote location 170 of an imaging suite, e.g., behind a shielded wall 172.

The imaging system 100 includes a floor mount or base 140 for supporting the imaging system 100 on a floor. A gantry 142 extends upwards from the floor mount 140 and rotatably supports both the tube head 208 and a support arm 210. The tube head 126 and support arm 124 are configured to rotate discretely from each other and may also be raised and lowered along a face 144 of the gantry 142 so as to accommodate patients of different heights. The x-ray source 122 is disposed within the tube head 208. Together, the tube head 126 and support arm 124 may be referred to as a C-arm 144.

A number of interfaces and display screens are disposed on the imaging system 100. These include a foot display screen 146, a gantry interface 148, a support arm interface 150, and a compression arm interface 152. In general the various interfaces 148, 150, and 152 may include one or more tactile buttons, knobs, switches, as well as one or more display screens, including capacitive touch screens with graphic user interfaces (GUIs) so as to enable user interaction with and control of the imaging system 100. In general, the foot display screen 146 is primarily a display screen, though a capacitive touch screen might be utilized if required or desired. In other examples, certain display screens 153 may be within a line of sight of the patient (standing at location P during imaging procedures).

The imaging system 100 also includes a guidance module 174. The guidance module may include one or more of a speaker 176 and a light-emitting element 178. Functionality associated with the guidance module 174 is described in more detail below. Here, the guidance module is depicted in the gantry 142, but may be disposed in other portions of the imaging system 100. In other examples, a portion of the guidance module 174 (e.g., the speaker 176) may be disposed in a direction generally facing the patient P, which may improve comprehension of verbal instructions or other sounds emitted therefrom. The light-emitting element 178 may be disposed on a rear portion of the gantry 142 which may help to illuminate surfaces within the imaging suite, e.g., effectively changing the ambient light therein, as explained in more detail below. A sensor S is depicted in the tube head 126 and may detect a position thereof and may communicate with the guidance module 174. In other examples, other sensors may be disposed in other locations of the imaging system 100 and/or may be used to detect various conditions of any of the components depicted in FIGS. 1A and 1B, or of other components found in an imaging system. An accessory A, examples of which are described below, may be remote from the housing of the imaging system 100, and may communicate via wired or wireless connections to the guidance module 174.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112.

Imaging procedures are often challenging for both the patient and the technologist. For the patient, the discomfort and anxiety associated with the compressive procedure. This discomfort may cause a patient to move during imaging, which can result in images that are blurred, has imaging artifacts or is otherwise insufficient for diagnostic purposes. If the image is insufficient, the patient would need retakes or additional images which could lead to further discomfort. In other instances, the patient may be asked to return back to the screening center after leaving the facility, which causes additional stress, anxiety and inconvenience for the patient. Further, patients are required to hold their breath during imaging procedures, so as to not adversely affect the quality of the resultant images. In other instances, the stress of the procedures may result in a patient inadvertently holding her breath, which can result in light-headedness or even fainting, especially during biopsy or other procedures. Some patients may be unable to hold their breath for a long period of time due to health conditions. In still other instances, patients may shallow breathe.

While technologists are trained to guide and reassure patients, the technologist is often focused on controlling the imaging procedure itself and may be distracted from giving regular directions. Also, it may be particularly difficult for technologists to communication with patients who have hearing challenges (or vision difficulties). For example, technologists typically ask a patient to hold their breath during emission of x-rays. It may be extremely difficult for the technologist to communicate that instruction from behind a shielded wall, as they control the procedure from the workstation (e.g., workstation 138 in FIG. 1A). These and other challenges may be addressed by incorporating guidance modules 174 into breast imaging systems. The guidance modules 174 may include one or more speakers, light-emitting elements, or other components that emit signals to help guide the patient during breast imaging procedures.

Figure 2:
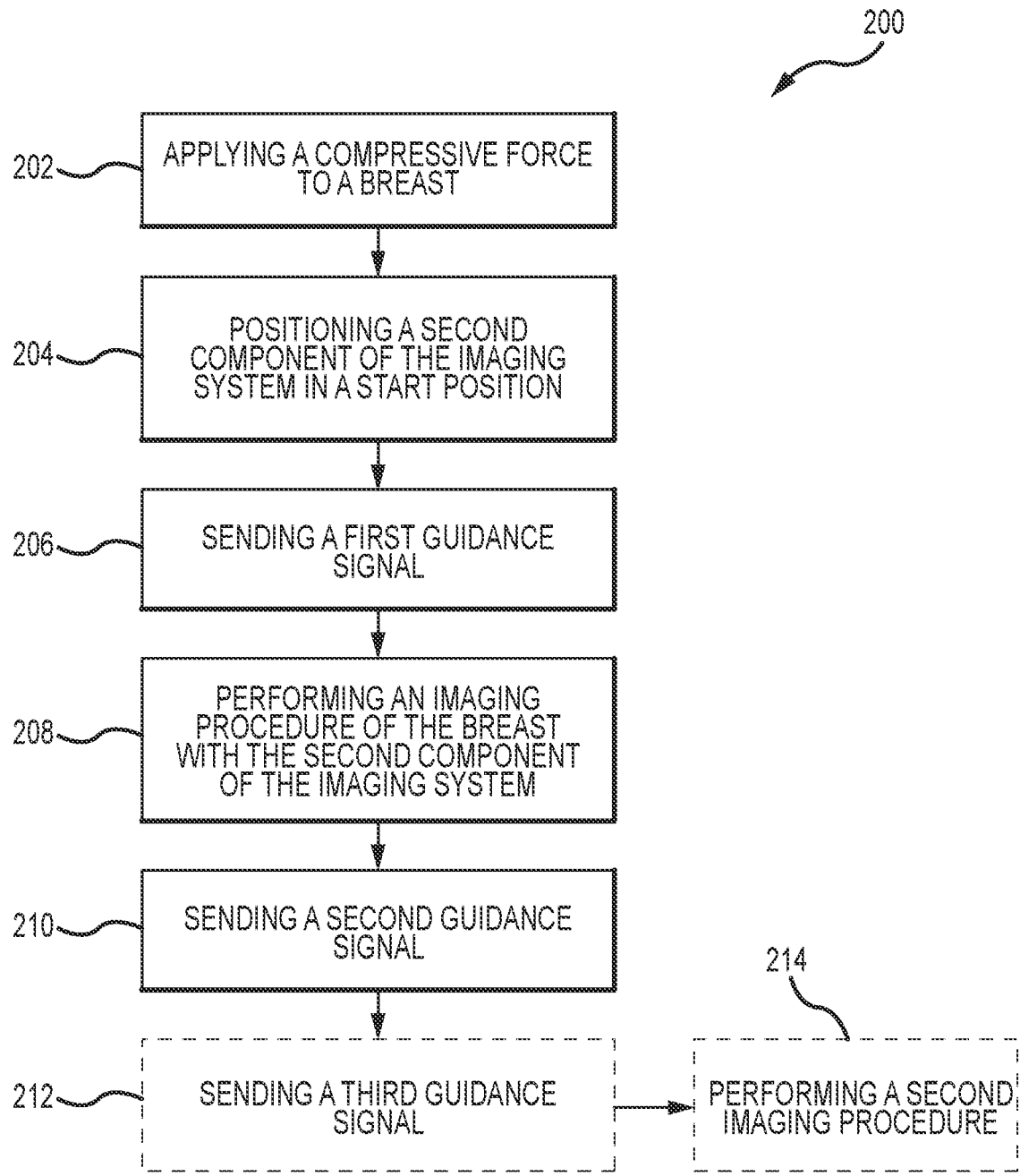
FIG. 2 depicts a method of providing guidance to a patient during breast imaging procedures.

FIG. 2 depicts a method 200 of providing guidance with a guidance module to a patient during breast imaging procedures. In operation 202, a compressive force is applied to a breast of a patient. Relevant to the imaging system depicted in FIGS. 1A and 1B, the compressive force is applied with the compression paddle and the support platform, with the compression paddle being lowered on the breast that is resting on the support platform. The technologist positions and manipulates the breast while the compression arm lowers the paddle onto the breast so as to compress, stabilize, and/or immobilize the breast. To avoid unnecessary exposure to x-ray radiation, the technologist then moves away from the patient, for example to a control system typically located in a location remote from the imaging system itself. This location may be in a different area of the imaging suite, typically behind a shielded wall. From the control system, the technologist may initiate an imaging procedure, such as a mammography or tomosynthesis procedure, or a so-called combo procedure, which performs both mammography and tomosynthesis procedures during a single breast compression. Other procedures, such as wide-angle tomosynthesis or computed tomography are contemplated. The technologist may then initiate the imaging procedure by setting any necessary parameters and pressing an activation or initiation button or switch. Upon initiation, a tube head (containing the x-ray source) of the imaging system may move to a start position, operation 204. This start position may be consistent with the start of a tomosynthesis imaging procedure (e.g., the tube head may move to a position tilted relative to the position of the breast on the platform). In another example, the tube head may move from a clearance position (where the tube head is positioned so as to improve technologist access to the breast) to a position where an image may be taken. This operation 204 also contemplates the tube head already being positioned in the start location when the imaging procedure is initiated.

Operation 206 includes sending, from the imaging system, a first guidance signal to the patient. In an example, a speaker on the guidance module of the imaging system may deliver audible instructions to the patient during a procedure. For example, the speaker may emit a guidance signal in the form of a voice command such as "HOLD YOUR BREATH", prior to beginning of the imaging procedure. This guidance signal may be timed precisely with a condition of one or more components of the imaging system (e.g., it may be timed to an emission of x-ray energy), so as to limit the amount of time that the patient must hold her breath. Since certain imaging procedures, e.g., tomosynthesis or wide-angle tomosynthesis, may take over about 2 seconds, over about 4 seconds, or over about 6 or more seconds to perform, this may be particularly useful. This may also be desirable, since the sounds associated with the imaging system may drown out instruction typically provided verbally from the technologist from a location remote from the imaging system and patient. Guidance signals in the form of light emissions may also be used to provide instruction to the patient. In one example, a light-emitting element of the guidance module may be disposed in a location within a line of sight of the patient. The patient may be instructed previously by the technologist to hold her breathe upon illumination of the light-emitting element. Again, this could be particularly advantageous for a patient with limited hearing, so they may hold their breath for the shortest amount of time, notwithstanding whether or not the technologist is nearby to provide a visual or other instruction. In this regard, the technologies described herein may obviate the need for the technologist to provide any instructions to the patient, or may remove the need for a technologist to create a communications scheme with a person who may be hard of hearing. This can enable the technologist to focus primarily on obtaining medically relevant x-ray images, while still having the patient act in such a way as to not reduce the quality of the images (e.g., by breathing at undesirable times).

As noted above, operation 206 may be timed relative to the imaging procedure, for example, the emission of x-ray energy towards the breast, so the patient will hold her breath for the minimum amount of time required. Accordingly, operation 208, performing an imaging procedure with the x-ray source, which in examples may be a single-emission imaging procedure (e.g., mammography) or a multi-emission imaging procedure (e.g., tomosynthesis). For the purposes of this example, however, a tomosynthesis imaging procedure is performed. Once the tomosynthesis imaging procedure is complete, a second guidance signal is sent, operation 210. In an example, if audible guidance signals are being used, the speaker may emit an instruction to "BREATHE" in operation 210. In combo imaging procedures (e.g., imaging procedures that perform both mammography and tomosynthesis during a single breast compression), operation 210 may be performed, for example, after the tube head reaches the end of its tomosynthesis sweep. The tube head may then return to its centered position above the breast, consistent with a cranial caudal position for mammography. At that time, prior to emission of the x-ray energy for the mammogram image, a third guidance signal may be sent, operation 212. This third guidance signal may be an audible or visual signal that indicates to the patient that she, once again, must hold her breath. In this example, operation 214, performing a second, different imaging operation, follows.

Although the guidance signals of the above method 200 are described generally as emissions of audible verbal signals and lights, other guidance signals may be utilized. In one example of alternative audible guidance signals, the patient may be previously instructed (e.g., by the technologist) to hold her breath while music plays, and that she may begin to breathe again when the music stops. Non-verbal guidance signals such as tones, chimes, or other sounds may be utilized. While any type of sound may be used, it may be desirable for pleasant, calming sounds to be utilized (e.g., soft bells). In general, however, any type of sound (verbal or non-verbal) may be utilized as required or desired for a particular application. It may be desirable for the sound emitting component (e.g., speaker) to be disposed on a patient-facing location of the imaging system, so sound is more easily directed at the patient. In addition to providing guidance to the patient, the technologies described herein also aim to soothe the patient during stressful or uncomfortable imaging or other procedures. In this regard, the playing of music may be utilized at key times. In addition to acting as a guidance signal, this music (or other sound) may help soothe or otherwise distract the patient, thus making the procedure more tolerable.

Guidance signals provided by light-emitting elements are described above as being within a line of sight of the patient. In another example, the light-emitting elements may be disposed in a location such that they are outside the line of sight of the patient. In that case, these lights may emit indirect light into the imaging suite in such a way so as to change the ambient light therein. This has been determined to help change or soothe the mood of a person within the room. As such, the guidance module may include a light-emitting element disposed outside a field of view of the patient. The light-emitting element may emit light at required or desired times during an imaging procedure, thereby providing guidance to the patient as to an action to take (e.g., inhaling, holding her breath, etc.). By emitting the light in a direction away from a patient (e.g., towards a wall at a rear of the imaging system gantry, towards a ceiling, etc.), the ambient light within the imaging suite may change. Softer, soothing colors may be utilized as both the guidance signal and to help relax the patient at key times. In addition to light color, changes in emission patterns (e.g., blinking, dimming, etc.) may be utilized to guide the patient to take certain actions.

Figure 3:
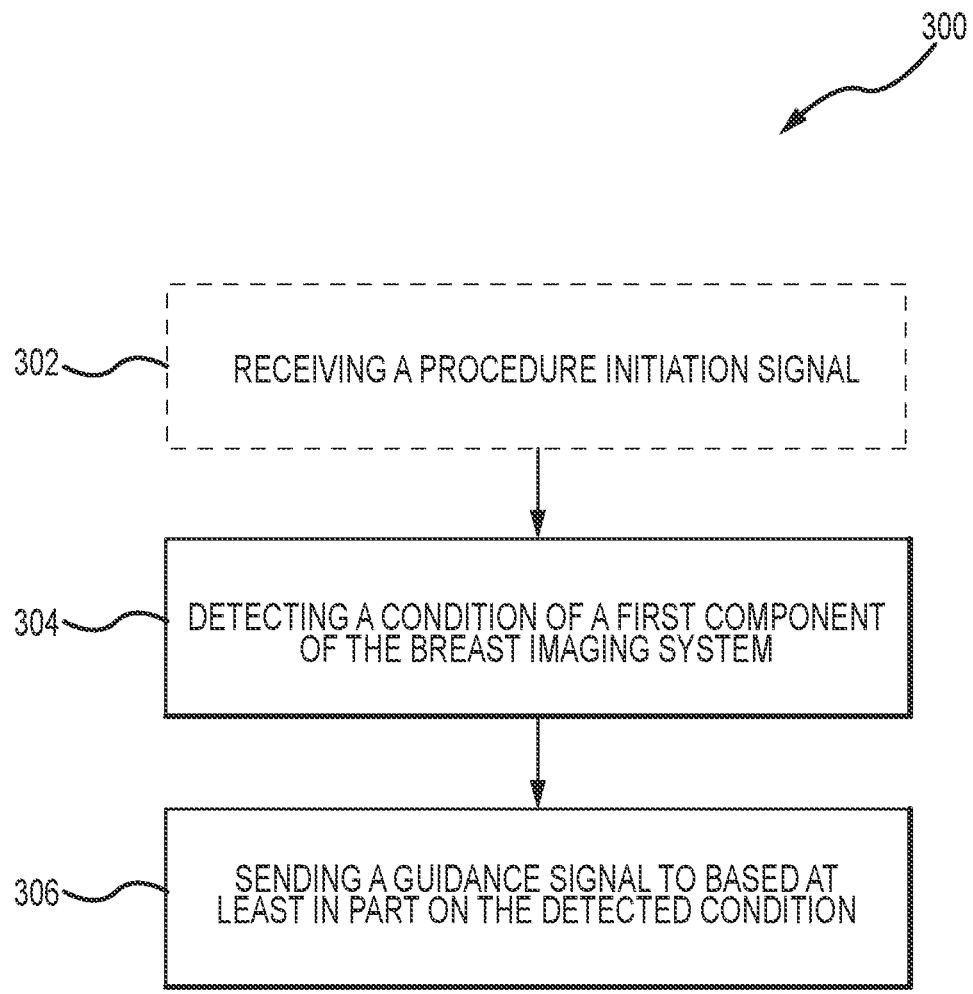
FIG. 3 depicts a method of providing guidance to a person with an imaging system based on one or more conditions detected by the imaging system.

The method 200 described above is directed to providing guidance signals from an imaging system to a patient during an imaging procedure. The technologies contemplated herein are not so limited, however. Rather, the technologies may be utilized to provide automated guidance from the imaging system to the patient based on one or more conditions detected by the imaging system. FIG. 3 depicts such a method 300, generally. The method 300 may, in some examples, begin with optional operation 302, receiving a procedure initiation signal. Examples of particular procedures are described herein, but are not limited only to those procedures. In general, this operation contemplates a signal received that initiates a detection sequence in the imaging system. In examples, the signal may be a POWER ON signal received as the imaging system is started, or may be the more specific example of a technologist initiating an imaging procedure. Other initiation signals are described herein. Flow continues to operation 304, where a condition of a component of the imaging system is detected. Based at least in part on this detected signal, operation 306, sending a guidance signal from the imaging system (e.g., in the form of an emitted light or sound), is performed. As is apparent from the above description, the method 200 of FIG. 2 is a more detailed version of the method 300 of FIG. 3. For example, operation 204 may correspond to operation 304, while operation 206 may correspond to operation 306.

The methods depicted in FIGS. 2 and 3 may be applied to provide guidance to a patient at other times during an imaging system, e.g., based on other detected conditions in the imaging system or of components associate with the imaging system. A number of contemplated examples are described below, and the application of the above methods thereto would be apparent to a person of skill in the art.

EXAMPLE 1

Stressed Breathing Detection

Accessories that may interface with the patient may be connected via wired or wireless connections to the guidance module of the imaging system. Such accessories may detect behaviors of the patient and may be used to initiate automatically guidance signals (as described herein) to the patient. Accessories may include an accelerometer or other component that may detect excess movement (consistent with shallow or so-called "panic" breathing), a flow meter that the patient may breathe through during an imaging procedure, a pulse oximeter, or other device. In that regard, the detected condition may be associated with a signal sent from the accessory. The signal may be processed at the guidance module and a relevant guidance signal may be emitted. Such a guidance signal may be verbal (e.g., "BREATHE DEEPLY", "RELAX", etc.), or another sound or a light. If a non-verbal guidance signal is used, the patient may have been instructed in advance that certain lights or sounds require particular responses from them such as, for example, normalizing their breathing.

EXAMPLE 2

Paddle Movement Detection

The compression arm or paddle may be fitted with a strain or other gauge(s) that may detect forces acting on the paddle that are in directions indicative of patient movement. Typically the forces acting upon the paddle and/or compression arm are substantially orthogonal to the breast support platform. Forces having components substantially parallel to the breast support platform may be indicative of a patient pulling away from the imaging system in an effort to escape discomfort. Upon detection of such a condition, a signal may be sent to the guidance system. Verbal guidance signals such as "LEAN FORWARD" may be emitted in response thereto. Other audible or visual guidance signals may also be directed towards the patient. For example, if the patient begins to pull away from the imaging system, a chime may sound. In another example, a light may begin to flash if the patient is standing in a manner that is undesirable (e.g., leaning away from the machine or leaning to one side) and may return to a constant emission once the patient returns to an acceptable position. Condition signals sent from cameras or other devices that can recognize patient positioning may also be utilized.

EXAMPLE 3

Biopsy Needle Position

The guidance signal technologies described herein can also be used to direct a patient to hold their breath and/or forcibly exhale during biopsy procedures. The condition detected may be associated with a position of a biopsy needle just prior to insertion into the breast and a signal associated therewith may be send to the guidance module. A guidance signal, e.g., in the form of an emitted light intended to indicate to the patient to not move or not breath, may then be emitted for the remainder of the procedure (e.g., until the biopsy needle is removed from the breast).

EXAMPLE 4

Advanced Breathing Guidance

During certain imaging procedures, it may be desirable to provide more advanced breathing guidance to a patient. For example, between portions of a combo imaging procedure (e.g., between a tomosynthesis sweep and a mammogram image acquisition), it may be desirable to guide the patient's breathing as the tube head returns to the mammography imaging position. In that regard, the detected condition may be the tube head reaching the end of the tomosynthesis sweep. As the tube head returns to the mammography imaging position, a guidance signal in the form of changes in light emission levels may guide the patient to breathe as the tube head moves. For example, the patient may be previously instructed to track their inhalation to gradually increasing light levels and to track their exhalation to gradually decreasing (e.g., dimming) light levels.

EXAMPLE 5

Guidance for Technologists

While the technologies described herein are designed primarily to aid the patient by providing signals to guide the patient during an imaging procedure, the technologies may also aid the technologist, e.g., in allowing the technologist to focus more on obtaining accurate images, without having to focus extensively on instructing and soothing the patient. For example, while information relevant to the compression procedure (applied pressure, for example) is typically displayed on one or more displays on the imaging system, the guidance signals emitted by the guidance module may also be utilized to guide the technologist. In a particular example, a light-emitting element disposed at the rear of the gantry (which may alter the ambient light within the imaging suite), may change from a first color to a second color when a compressive force to the breast reaches a predetermined amount. Thus, the condition (applied force) detected by a sensor associated with the compression arm or compression paddle. A signal may then be sent to the guidance module and a resulting guidance signal may be emitted. This may enable the technologist to focus more on maintaining a position of the breast to ensure proper imaging, without having to constantly look at a display to read the compressive force applied. Other conditions that require a technologist to take certain actions may be detected and guidance signals emitted in response thereto.

EXAMPLE 6

Training Aid for Technologists

The detection and guidance signal technology may also be utilized as a training aid for technologists. In examples, technologists practice some aspects of imaging procedures on a breast phantom. These may include proper positioning of the breast, applications of compressive force, etc. Optical detectors such as cameras, position sensors, or other sensors may be directed to view or otherwise detect conditions of the breast support platform. In the case of cameras, for example, image recognition may be used to detect proper positioning of the phantom and signals associated with proper positioning may be sent to the guidance module. Guidance signals in the form of emitted lights may change depending on the phantom position (e.g., red lights for an improperly positioned phantom, green for a properly positioned phantom). This may help the technologist learn to properly position a breast.

EXAMPLE 7

Guidance for Technicians

The technology described herein may also be used to guide a technician during service or calibration procedures. For example, the positioning of the x-ray source within the tube head can be particularly challenging to ensure proper alignment with the detector. A technician may adjust the position of the x-ray source and when the proper position is reached, a signal associated with this detected condition may be sent to the guidance module. In response, a guidance signal in the form of an emitted sound or emitted light may signal to the technician that the proper location has been reached.

Thus, the audible and visual guidance signals described generally above may improve both patient, technologist, and/or technician experience during imaging and other procedures. Specific examples and applications of the above-described technologies are described herein. These specific examples should not be viewed as limiting, however. Other applications consistent with the above are contemplated and would be apparent to a person of ordinary skill in the art upon reading this entire disclosure.

Figure 4:
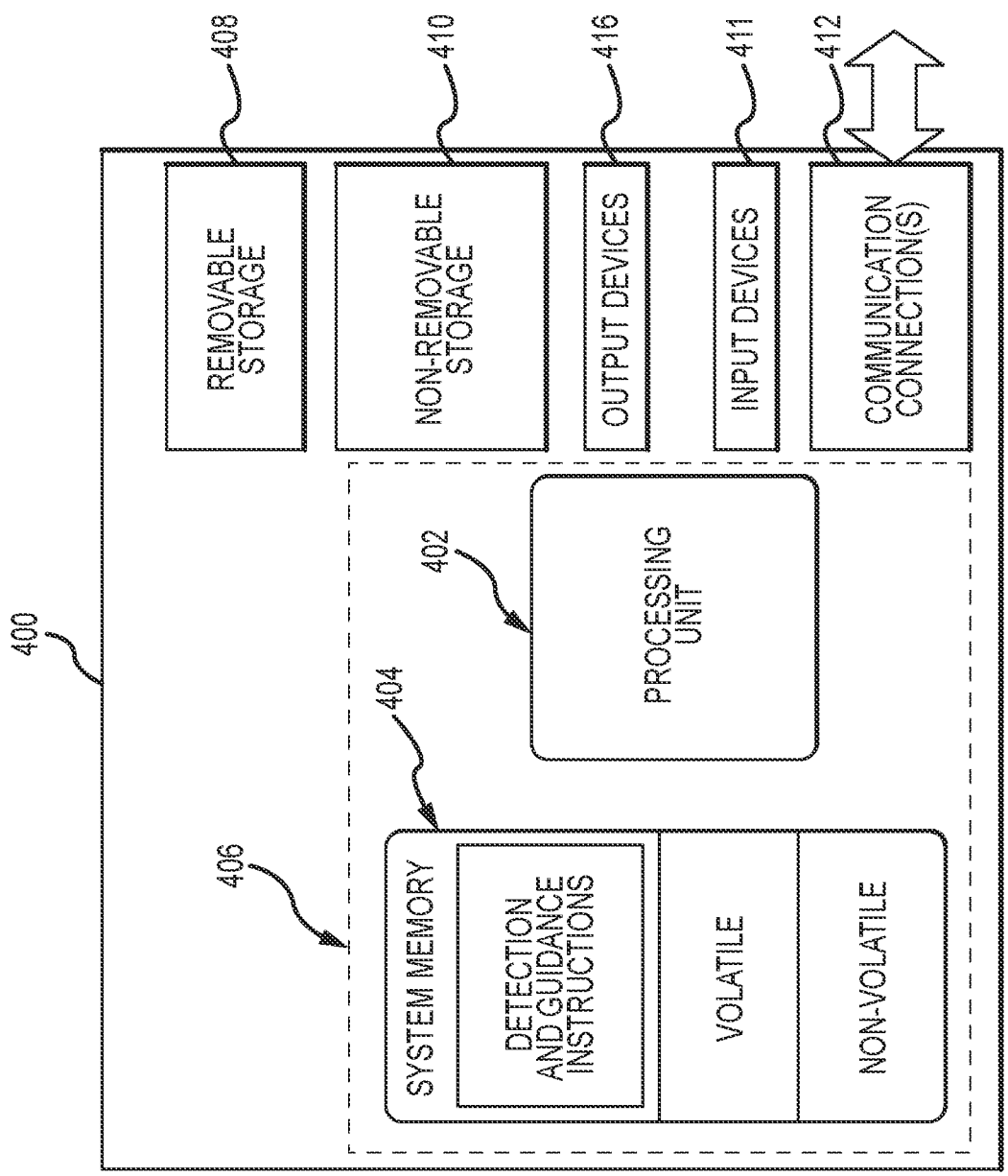
FIG. 4 depicts an example of a suitable operating environment in which one or more of the present examples can be implemented.

FIG. 4 illustrates one example of a suitable operating environment 400 in which one or more of the present examples can be implemented. This operating environment may be incorporated directly into the visualization systems disclosed herein, or may be incorporated into a computer system discrete from, but used to control the breast imaging systems described herein. Such as computer system may be, e.g., the work station depicted in FIG. 1A. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 400 typically includes at least one processing unit 402 and memory 404. Depending on the exact configuration and type of computing device, memory 404 (storing, among other things, instructions to detect conditions of one or more components of an imaging system and emit appropriate guidance signals based thereon, or perform other methods disclosed herein) can be volatile (such as RAM), non-volatile (such as ROM, flash memory, etc.), or some combination of the two. This most basic configuration is illustrated in FIG. 4 by dashed line 406. Further, environment 400 can also include storage devices (removable, 408, and/or non-removable, 410) including, but not limited to, magnetic or optical disks or tape. Similarly, environment 400 can also have input device(s) 414 such as touch screens, keyboard, mouse, pen, voice input, etc., and/or output device(s) 416 such as a display, speakers, printer, etc. Also included in the environment can be one or more communication connections 412, such as LAN, WAN, point to point, Bluetooth, RF, etc.

Operating environment 400 typically includes at least some form of computer readable media. Computer readable media can be any available media that can be accessed by processing unit 402 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 400 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 400 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 400 is part of a network that stores data in remote storage media for use by the computer system 400.

Figure 5:
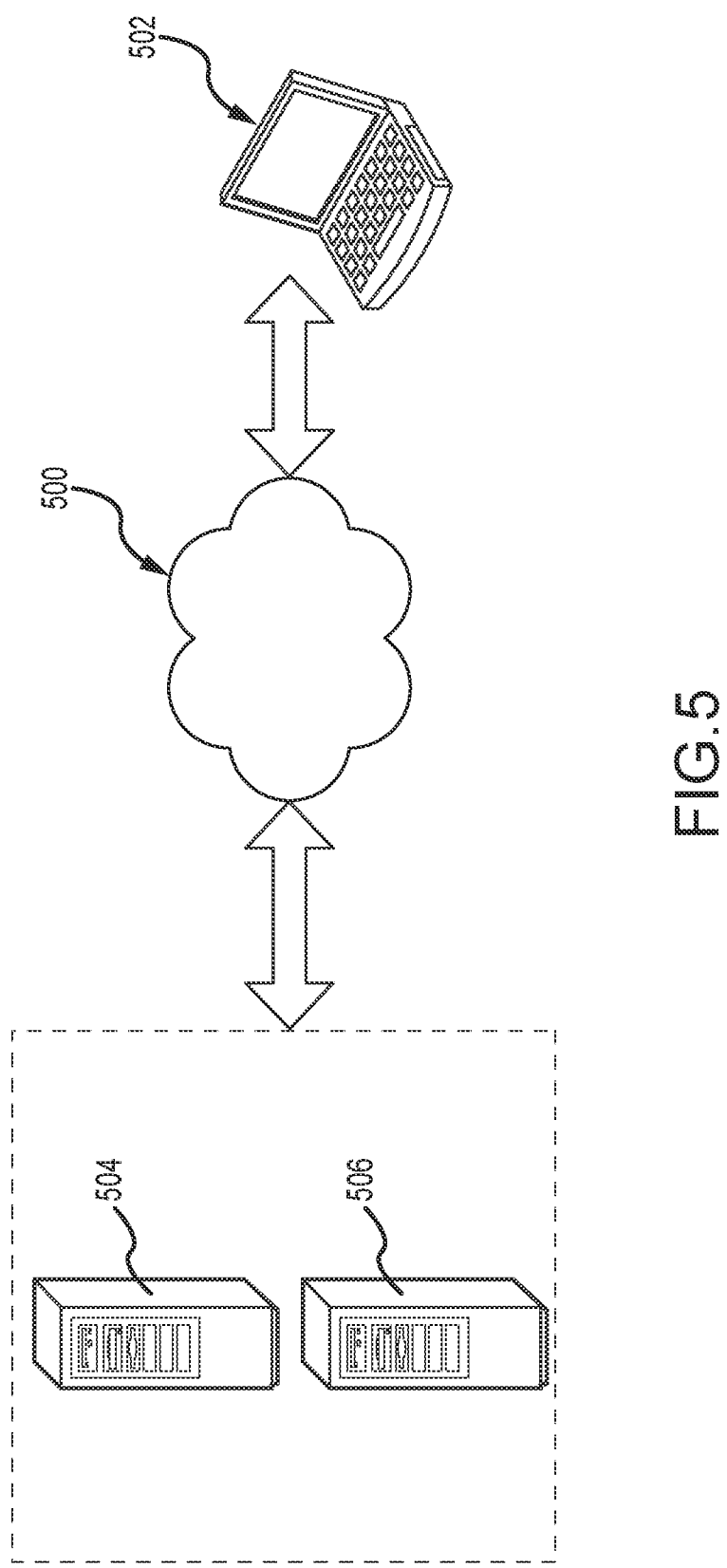
FIG. 5 depicts an example of a network in which the various systems and methods disclosed herein may operate.

FIG. 5 is an embodiment of a network 500 in which the various systems and methods disclosed herein may operate. In embodiments, a client device, such as client device 502, may communicate with one or more servers, such as servers 504 and 506, via a network 500. In embodiments, a client device may be a standalone imaging system (e.g., imaging system 100 depicted in FIG. 1A) that includes all the functionality described herein. The client device may also include or incorporate a laptop, a personal computer, a smart phone, a PDA, a netbook, or any other type of computing device, such as the computing device in FIG. 4. In examples, such a client device may be connected to an imaging system. In embodiments, servers 504 and 506 may also be any type of computing device, such as the computing device illustrated in FIG. 4. Network 500 may be any type of network capable of facilitating communications between the client device and one or more servers 504 and 506. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 504 may be employed to perform the systems and methods disclosed herein, such as the methods for imaging discussed herein. Client device 502 may interact with server 504 via network 500. In further embodiments, the client device 502 may also perform functionality disclosed herein, such as scanning and image processing, which can then be provided to servers 504 and/or 506.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of imaging a breast of a patient using an imaging system, the method comprising:
    applying, with a first component of the imaging system, a compressive force to the breast;
    positioning a second component of the imaging system in a start position;
    sending, from the imaging system, a first guidance signal;
    performing an imaging procedure of the breast with the second component of the imaging system; and
    subsequent to performing the imaging procedure, sending a second guidance signal.

2. The method of claim 1, wherein the first guidance signal comprises at least one of a visible light and an audible noise.

3. The method of claim 2, wherein the first guidance signal comprises a light of a first color and wherein the second guidance signal comprises a light of a second color different than the first color.

4. The method of claim 1, wherein performing the imaging procedure comprises emitting a single x-ray emission.

5. The method of claim 1, wherein performing the imaging procedure comprises emitting a plurality of x-ray emissions.

6. The method of claim 2, wherein the first guidance signal comprises a first sound and the second guidance signal comprises a second sound different than the first sound.

7. The method of claim 2, wherein the first guidance signal comprises the audible noise and the second guidance signal causes a termination of the audible noise.

8. The method of claim 1, further comprising, during performance of the imaging procedure, sending a third guidance signal.

9. A breast imaging system comprising:
    a gantry comprising a patient side and a rear;
    a compression system movably secured to the patient side of the gantry, wherein the compression system comprises a breast support platform and a compression arm movable relative to the breast support platform;
    a tube head rotatably connected to the gantry; and
    a patient guidance module for sending at least one of a visual guidance signal and an audible guidance signal to the patient when a breast of the patient is compressed by the compression system.

10. The breast imaging system of claim 9, wherein the patient guidance module comprises a light emitting element disposed on the rear of the gantry.

11. A method of guiding a patient action during a procedure with a breast imaging system, the method comprising:
    detecting a condition of a first component of the breast imaging system, wherein at least a portion of the breast imaging system is in contact with a breast of the patient; and
    sending, from the breast imaging system, a guidance signal to the patient based at least in part on the detected condition, wherein the guidance signal is associated with an action to be taken by the patient.

12. The method of claim 11, further comprising, prior to detecting the condition, receiving, at the breast imaging system, a procedure initiation signal, wherein the procedure initiation signal is sent from a physical location remote from the breast imaging system.

13. The method of claim 11, further comprising, subsequent to receiving the procedure initiation signal and prior to detecting the condition, moving a second component of the breast imaging system to a start position.

14. The method of claim 13, wherein the first component is disposed within the second component.

15. The method of claim 11, wherein the first component comprises an x-ray tube.

16. The method of claim 15, wherein the detected condition comprises a voltage reading.

17. The method of claim 11, wherein the guidance signal comprises an audible sound.

18. The method of claim 17, wherein the audible sound is non-verbal.

19. The method of claim 11, wherein the guidance signal is an emitted light.

20. The method of claim 19, wherein the emitted light is emitted from a light emitting element outside a line of sight of the patient when the portion of the breast imaging system is in contact with the breast of the patient.

* * * * *